(12) United States Patent
Goodwin (10) Patent No.: US 10,092,214 B2
(45) Date of Patent: Oct. 9, 2018

(54) MAGNETIC RESONANCE IMAGING MARKER

(71) Applicant: Randy Goodwin, Dade City, FL (US)

(72) Inventor: Randy Goodwin, Dade City, FL (US)

( * ) Notice: Subject to any disclaimer, the term of this patent is extended or adjusted under 35 U.S.C. 154(b) by 115 days.

(21) Appl. No.: 13/781,665

(22) Filed: Feb. 28, 2013

(65) Prior Publication Data

US 2014/0243655 A1   Aug. 28, 2014

(51) Int. Cl.
*A61B 5/055* (2006.01)
*A61B 90/00* (2016.01)

(52) U.S. Cl.
CPC .............. *A61B 5/055* (2013.01); *A61B 90/39* (2016.02); *A61B 2090/3954* (2016.02)

(58) Field of Classification Search
CPC .. A61B 2090/3954; A61B 5/055; A61B 90/39
See application file for complete search history.

(56) References Cited

U.S. PATENT DOCUMENTS

| | | | |
|---|---|---|---|
| 2005/0215922 A1* | 9/2005 | Tsonton et al. | 600/566 |
| 2008/0093245 A1* | 4/2008 | Periasamy et al. | 206/438 |
| 2011/0004094 A1* | 1/2011 | Stubbs et al. | 600/424 |

* cited by examiner

*Primary Examiner* — Ruth S Smith
(74) *Attorney, Agent, or Firm* — Cygnet IP Law, P.A.; Stephen W. Aycock, II (57) ABSTRACT

An imaging marker including a body portion having a cavity in the shape of a letter is described. The cavity can be filled with a liquid containing a substance that illuminates during an imaging process. The imaging marker can also include a first end cap and a second end cap. The first end cap can be configured to be placed on a first end of the body portion, and the second end cap can be configured to be placed on a second end of the body portion.

5 Claims, 10 Drawing Sheets

MAGNETIC RESONANCE IMAGING MARKER

FIELD

Embodiments relate generally to markers used in medical imaging and, more particularly, to markers used in magnetic resonance imaging.

BACKGROUND

When obtaining images of a patient's body, it may be helpful to have a marker in the image to indicate a reference for the physician such as a radiologist to use when evaluating the image. For example, it may be helpful to have an indication of whether an image is taken from the left side or the right side of a patient's body. Conventional imaging markers may only provide an indication of whether the marker was present or not. For example, a marker may be a circle or a square-shaped marker that can only indicate whether the marker was present or not. Further, conventional markers are often applied during x-ray imaging and other types of imaging where the marker will show up in a 2D image. When obtaining images in a magnetic resonance imaging (MRI) system, images are obtained in two dimensional "slices" that, when viewed together, form a three dimensional picture of a portion of the patient's body. Conventional markers may not appear in all of the image slices obtained during MRI imaging.

Embodiments were conceived in light of the above-mentioned problems and limitations, among other things.

SUMMARY

Some implementations can include an imaging marker with a body portion having a cavity in the shape of a letter, wherein the cavity can be filled with a liquid containing a substance that illuminates during an imaging process. The imaging marker can also include a first end cap and a second end cap. The first end cap can be configured to be placed on a first end of the body portion, and the second end cap can be configured to be placed on a second end of the body portion.

The solution can contain gadolinium. The imaging marker is configured to be used in a magnetic resonance imaging process. The cavity of the body portion is shaped in the form of a letter. For example, the cavity of the body portion is formed generally into a shape of a letter L or a letter R, for right or left side. In general, any letters or shapes may be used for the markers as long as the convention of which letter or symbol corresponds to which side of the body is known and is used consistently.

Some implementations can include a magnetic resonance imaging marker system comprising a first marker having a liquid filled cavity, wherein the cavity is formed into a first shape, and a second marker having a liquid filled cavity, wherein the cavity is formed into a second shape different from the first shape.

The liquid can contain gadolinium or other substance that illuminates during an MRI process or other imaging process. The imaging marker can be configured to be used in a magnetic resonance imaging process. The cavity of the first marker and the cavity of the second marker are each shaped in the form of a letter. The first shape is formed generally into a shape of a letter L. The second shape is formed generally into a shape of a letter R.

Some implementations can include a method of making an imaging marker. The method can include providing a body portion having a cavity formed into a shape and providing a first end cap. The method can also include providing a second end cap and providing a liquid that illuminates under an imaging process.

The liquid can be placed into the cavity of the body portion and the first end cap and the second end cap are placed onto respective ends of the body portion so as to seal the liquid inside the cavity of the body portion. The liquid can contain gadolinium.

The imaging marker can be configured to be used in a magnetic resonance imaging process. The cavity can be formed in the shape of a letter. For example, the cavity can be formed generally into a shape of a letter L or a letter R, or the like.

DETAILED DESCRIPTION

Figure 1:
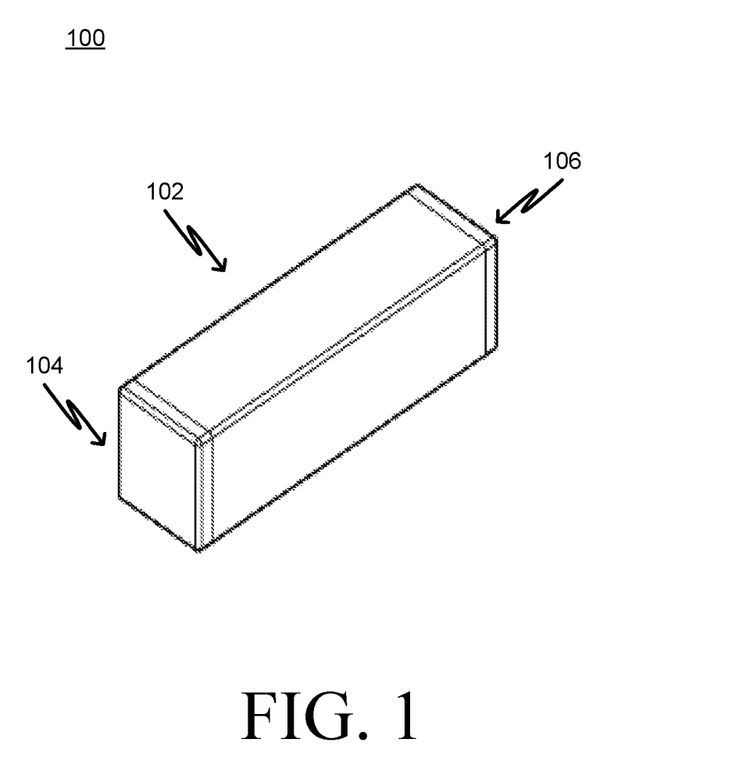
FIG. 1 shows a perspective view of a right side MRI marker in accordance with at least one embodiment.

FIG. 1 shows an example MRI marker 100 adapted to indicate a right side of a person's body as indicated by the letter R appearing in a three-dimensional extension through the body of marker 100. The right side MRI marker 100 had a body portion 102, a first end cap 104, and a second end cap 106. Also, the body portion is filled with a liquid (not shown) that illuminates during the MRI process.

The end caps 104 and 106 in the body portion 102 can be formed from any suitable material such as plastic or wood. For example, the end caps 104 and 106 in the body portion 102 may be formed from a stereo lithography resin such as Somos Next manufactured by DSM. Any material that exhibits suitable properties such as invisibility to the MRI process, durability, and safety for use around patients can be used. The fluid that fills the interior cavity of the body portion 102 can be any type of fluid that illuminates in the MRI process. For example, fluids containing gadolinium can be used. Some commercial examples of gadolinium include Multihance, Magnevist, Prohance, Omniscan, Gadavist, and/or the like. Gadolinium is used to produce a bright signal intensity when exposed to MRI scanning techniques. The composition of the fluid can be a mixture of gadolinium and another liquid; for example, gadolinium can be mixed with a sodium chloride solution. In an example embodiment, 2 ml of Multihance can be mixed with 50 ml of sodium chloride solution. Various ratios of gadolinium to sodium chloride can be used. For example, rations of four, six, eight and 10 ml of gadolinium to 50 ml of sodium chloride solution can be used. It will be appreciated that other substances and/or concentrations can be used, the substances and concentrations discussed above are intended to be non-limiting examples.

Figure 2:
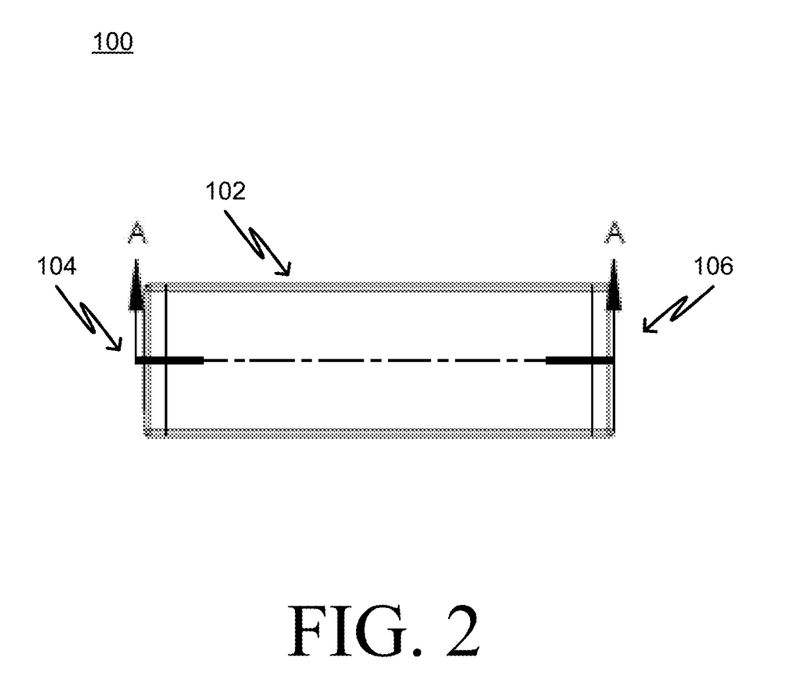
FIG. 2 shows a plan view of a right side MRI marker in accordance with at least one embodiment.
Figure 3:
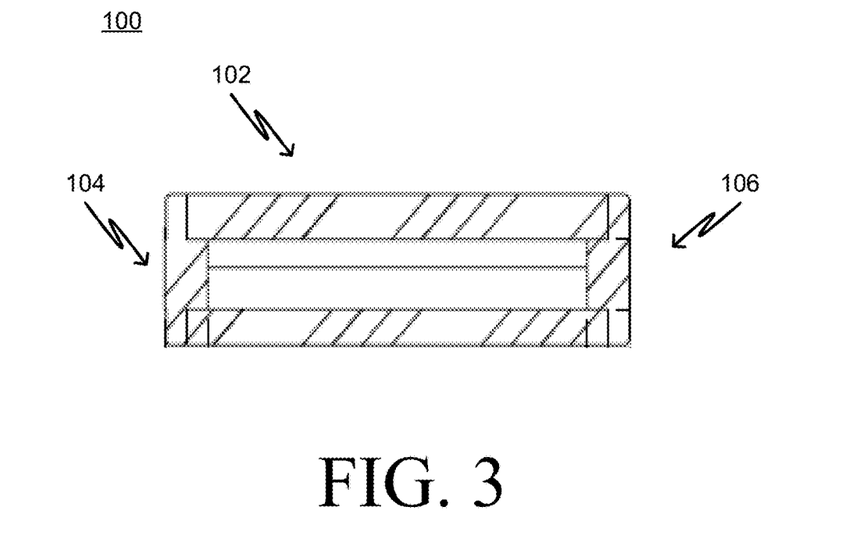
FIG. 3 shows a cross-sectional view of a right side MRI marker in accordance with at least one embodiment.

FIG. 2 shows a plan view of the right side MRI marker 100. FIG. 3 shows a cross-sectional view of the right side MRI marker 100 taken along line A-A shown in FIG. 2.

Figure 4:
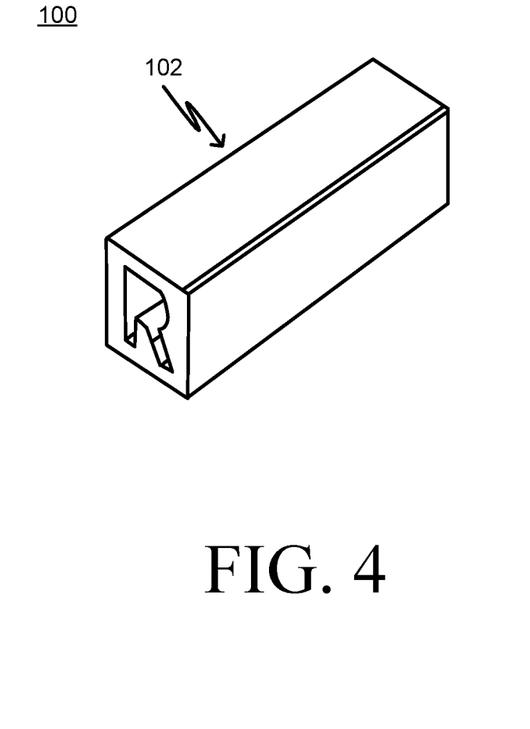
FIG. 4. Shows a perspective view of the interior of an MRI marker in accordance with at least one embodiment.

FIG. 4 shows a perspective view of body section 102 of the right side MRI marker 100. As can be seen in FIG. 4, there is a cavity formed throughout the body section 102 in generally the shape of a capital letter R to indicate right side.

Figure 5:
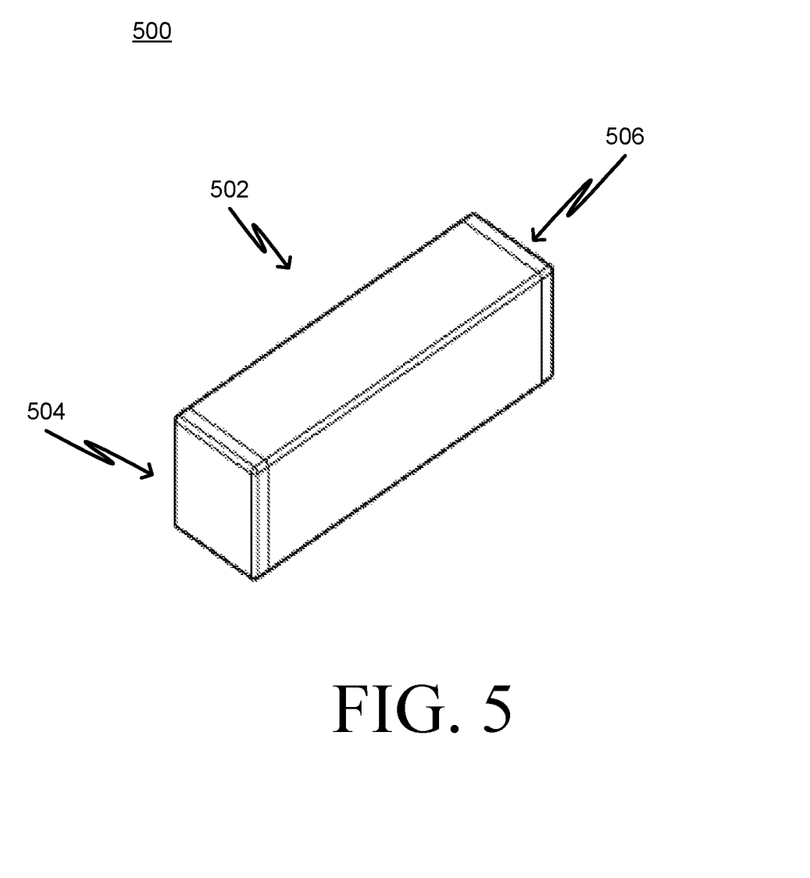
FIG. 5 shows a perspective view of a left side MRI marker in accordance with at least one embodiment.
Figure 6:
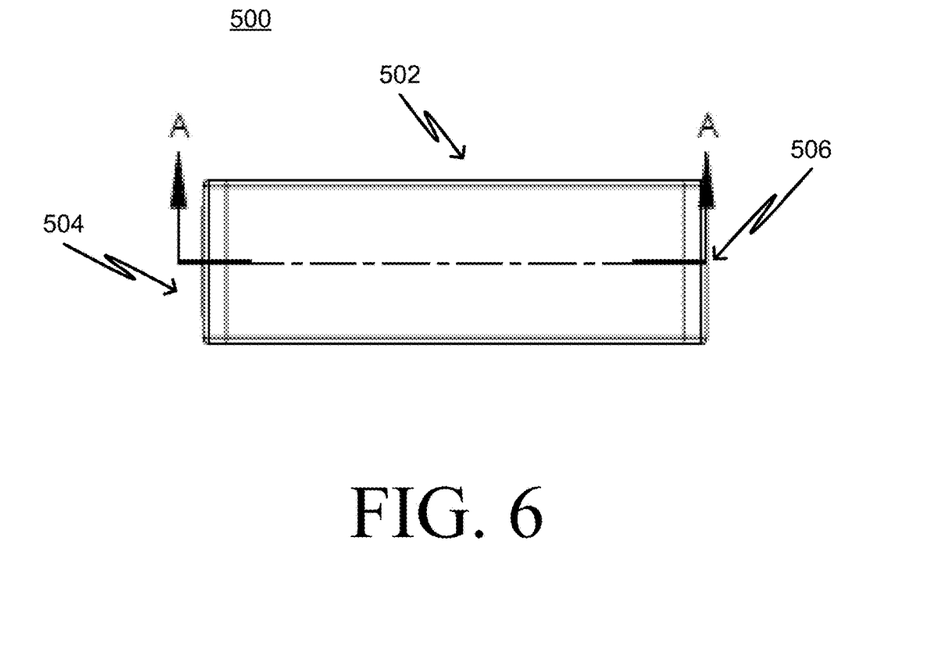
FIG. 6 shows a plan view of a left side MRI marker in accordance with at least one embodiment.
Figure 7:
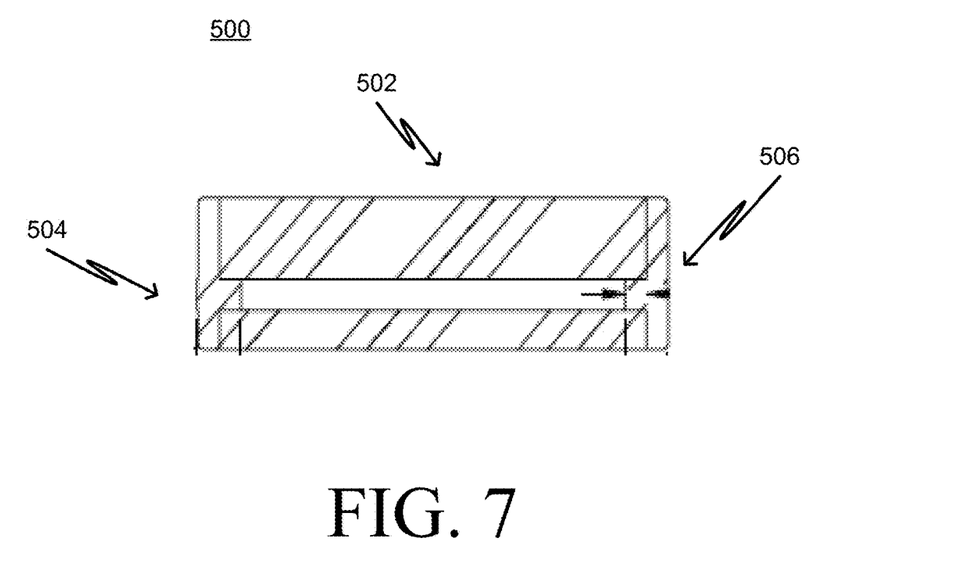
FIG. 7 shows a cross-sectional view of a left side MRI marker in accordance with at least one embodiment.
Figure 8:
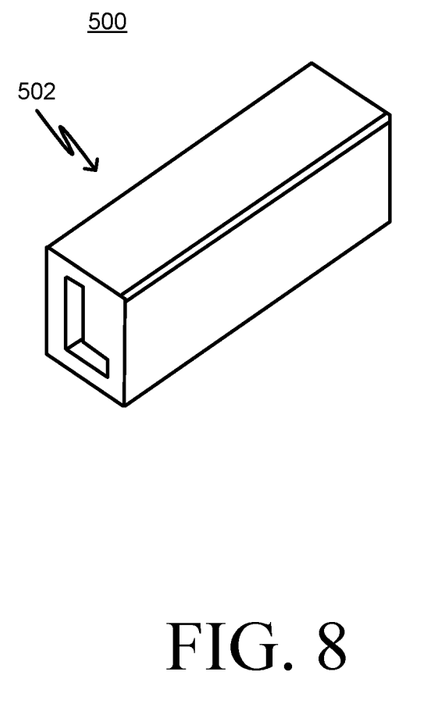
FIG. 8 shows a perspective view of an interior portion of a left side marker in accordance with at least one embodiment.

FIG. 5 is a perspective view of an example left side MRI marker 500, having a body portion 502, a first end cap 504, and a second end cap 506. FIG. 6 shows a plan view of the left side MRI marker 500. FIG. 7 shows a cross sectional view of the left side MRI marker 500 along line A-A shown in FIG. 6. FIG. 8 shows a perspective view of the body portion 502 of a left side MRI marker 500. As can be seen in FIG. 8, there is a cavity extending through the body portion 502 in generally the shape of a capital letter L to indicate the left side. The left side MRI marker 500 can be made using plastics and solutions as discussed above regarding the right side MRI marker 100.

Figure 9:
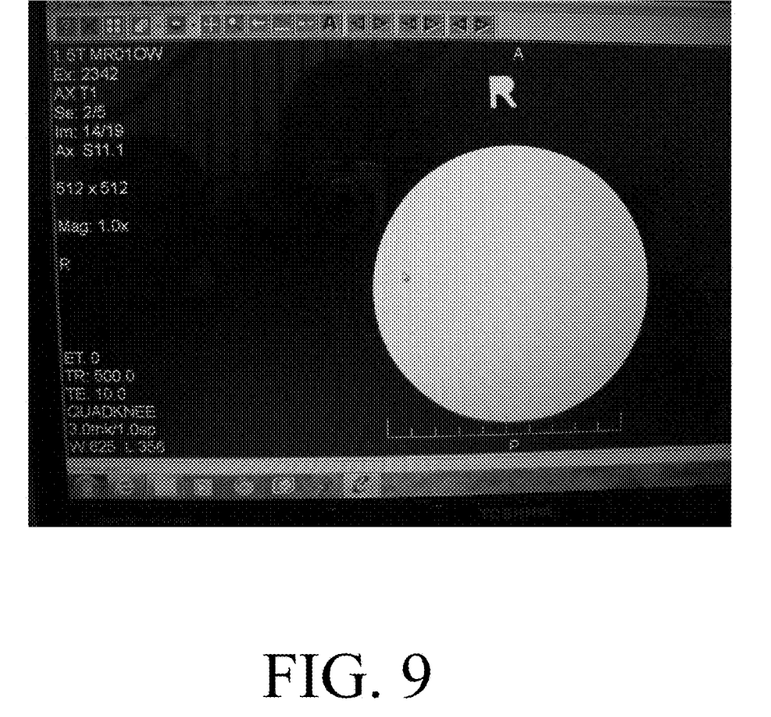
FIG. 9 shows an example MRI image having a right side MRI marker in accordance with at least one embodiment.

FIG. 9 shows an example MRI image in which a right side MRI marker (e.g., such as that shown in FIG. 1).

Figure 10:
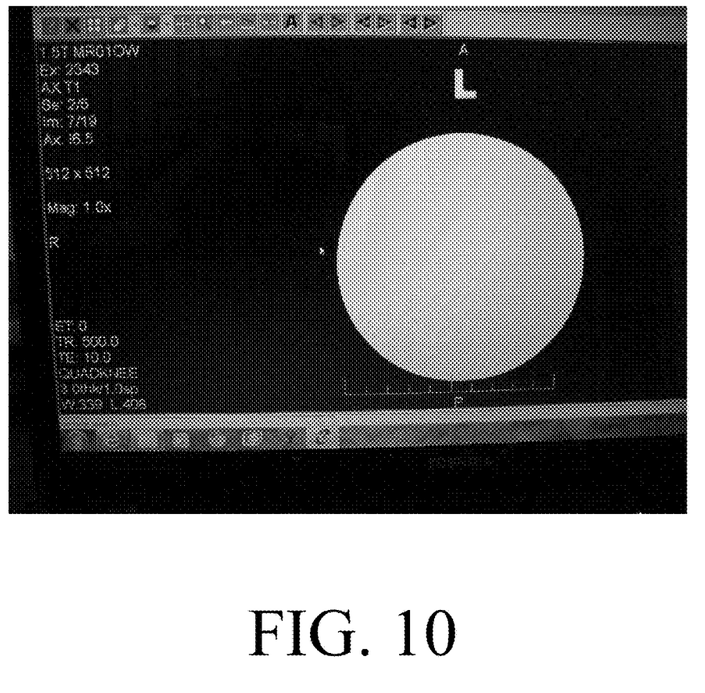
FIG. 10 shows an example MRI image having a left side MRI marker in accordance with at least one embodiment.

FIG. 10 shows an example MRI image having a left side MRI marker (e.g., left side MRI marker 500).

It is, therefore, apparent that there is provided, in accordance with the various embodiments disclosed herein, an imaging marker system and apparatus.

While the disclosed subject matter has been described in conjunction with a number of embodiments, it is evident that many alternatives, modifications and variations would be, or are, apparent to those of ordinary skill in the applicable arts. Accordingly, Applicant intends to embrace all such alternatives, modifications, equivalents and variations that are within the spirit and scope of the disclosed subject matter.

What is claimed is:

1. An imaging marker to mark magnetic resonance images, the imaging marker comprising:
   a body portion having a cavity with a cross-sectional shape of one of a capital letter L and a capital letter R, wherein the cavity extends throughout the body portion, wherein the body portion comprises a material that is invisible to a magnetic resonance imaging process, and wherein the cavity is filled with a liquid solution containing a substance that illuminates during the magnetic resonance imaging process;
   a first end cap disposed on a first end of the body portion; and
   a second end cap disposed on a second end of the body portion.

2. The imaging marker of claim 1, wherein the solution contains gadolinium.

3. A magnetic resonance imaging marker kit comprising:
   a plurality of markers,
   wherein the plurality of markers includes a first marker having a body portion and a liquid filled cavity extending throughout the body portion, wherein the liquid filled cavity comprises a cross-sectional shape of a capital letter L, wherein the liquid filled cavity is filled with a solution containing gadolinium, and wherein the first marker includes a first end cap disposed on a first end of the body portion and a second end cap disposed on a second end of the body portion; and
   wherein the plurality of markers further includes a second marker having a body portion and a liquid filled cavity extending throughout the body portion, wherein the liquid filled cavity comprises a cross-sectional shape of a capital letter R, and wherein the liquid filled cavity is filled with a solution containing gadolinium; and wherein the second marker includes a first end cap disposed on a first end of the body portion and a second end cap disposed on a second end of the body portion.

4. A method of making an imaging marker, the method comprising:
   providing a body portion having a cavity extending throughout the body portion, wherein the cavity comprises a cross-sectional shape of one of a capital letter L and a capital letter R, wherein the body portion comprises a material that is invisible to a magnetic resonance imaging process;
   providing a first end cap configured to fit onto a first end of the body portion;
   providing a second end cap configured to fit onto a second end of the body portion; and
   providing a liquid that illuminates under the magnetic resonance imaging process,
   placing the liquid into the cavity of the body portion; and
   placing the first end cap and the second end cap onto respective ends of the body portion so as to seal the liquid inside the cavity of the body portion.

5. The method of claim 4, wherein the liquid contains gadolinium.

* * * * *